US005532142A

United States Patent [19]
Johnston et al.

[11] Patent Number: 5,532,142
[45] Date of Patent: Jul. 2, 1996

[54] METHOD OF ISOLATION AND PURIFICATION OF FUSION POLYPEPTIDES

[75] Inventors: Stephen A. Johnston, Dallas, Tex.; William G. Dougherty, Philomath, Oreg.

[73] Assignees: Board of Regents, the University of Texas System, Austin, Tex.; State of Oregon, The, Acting By and Through the Oregon State System of Higher Education, on Behalf of Oregon State University, Corvallis, Oreg.

[21] Appl. No.: 21,603

[22] Filed: Feb. 12, 1993

[51] Int. Cl.⁶ .............................. C12N 9/52; C12P 21/00
[52] U.S. Cl. ...................... 435/69.1; 435/69.7; 435/219
[58] Field of Search .................................. 435/69.1, 69.7, 435/183, 219

[56] References Cited

U.S. PATENT DOCUMENTS

| | | | |
|---|---|---|---|
| 5,162,601 | 11/1992 | Slightom | 800/205 |
| 5,179,007 | 1/1993 | Jarvis et al. | 435/68.1 |
| 5,221,619 | 6/1993 | Itakura et al. | 435/69.4 |

FOREIGN PATENT DOCUMENTS

| | | |
|---|---|---|
| 12709/88 | 9/1988 | Australia. |
| 0293249 | 11/1988 | European Pat. Off.. |
| 0434605 | 6/1991 | European Pat. Off.. |
| WO84/03103 | 8/1994 | WIPO. |

OTHER PUBLICATIONS

Rorrer et al., *J. Gen. Virol.*, 73:775–783, 1992.

Allison et al., "The Nucleotide Sequence of the Coding Region of Tobacco Etch Virus Genomic RNA: Evidence for the Synthesis of a Single Polyprotein," *Virology*, 154:9–20, 1986.

Carrington et al., "A Second Proteinase Encoded by a Plant Potyvirus Genome," *The EMBO Journal*, 8(2):365–370, 1989.

Carrington and Dougherty, "A Viral Cleavage Site Cassette: Identification of Amino Acid Sequences Required for Tobacco Etch Virus Polyprotein Processing," *Proceedings of the National Academy of Science, USA*, 85:3391–3395, 1988.

Carrington and Dougherty, "Small Nuclear Inclusion Protein Encoded by a Plant Potyvirus Genome is a Protease," *Journal of Virology*, 61(8):2540–2548, 1987.

Dahlman et al., "High Level Expression in *Escherichia coli* of the DNA-Binding Domain of the Glucocorticoid Receptor in a Functional Form Utilizing Domain-Specific Cleavage of a Fusion Protein," *The Journal of Biological Chemistry*, 264(2):804–809, 1989.

Dougherty et al., "Biochemical and Mutational Analysis of a Plant Virus Polyprotein Cleavage Site," *The EMBO Journal*, 7(5):1281–12887, 1988.

Guan and Dixon, "Eukaryotic Proteins Expressed in *Escherichia coli*: An Improved Thrombin Cleavage and Purification Procedure of Fusion Proteins with Glutathione S-Transferase," *Analytical Biochemistry*, 192:262–267, 1991.

Montgomery et al., "Expression of an Autoprocessing CAT-HIV-1 Protinase Fusion Protein: Purification to Homogeneity of the Released 99 Residue Protinase," *Biochemical and Biophysical Research Communications*, 175(3):784–794, 1991.

Parks et al., "Cleavage Profiles of Tobacco Etch Virus (TEV)-Derived Substrates Mediated by Precursor and Processed Forms of the TEV NIa Proteinase," *Journal of General Virology*, 73:149–155, 1992.

Taylor and Drickamer, "Carbohydrate-Recognition Domains as Tools for Rapid Purification of Recombinant Eukaryotic Proteins," *Biochemistry Journal*, 274:575–580, 1991.

Waldenström et al., "Synthesis and Secretion of a Fibrinolytically Active Tissue-Type Plasminogen Activator Variant in *Escherichia coli*," *Gene*, 99:243–248, 1991.

Parks et al., Virology 182:17–27 (1991).

Uhlen, M. et al.; Meth. Enzymol. 185:129–143 (1990).

Smith, M. C. et al.; J. Biol. Chem. 263:7215 (1988).

Restrepo-Hartwig et al., J. Virol. 66:5662–5666 (1992).

Dougherty et al., Virology 172:302–310 (1989).

Dougherty et al., Virology 183:449–456 (1991).

Louis et al., Eur. J. Biochem. 199:361–369 (1991).

Menendez-Arias et al., J. Biol. Chem. 267:24134–24139 (1992).

*Primary Examiner*—Robert A. Wax
*Assistant Examiner*—Eric Grimes
*Attorney, Agent, or Firm*—Arnold, White & Durkee

[57] ABSTRACT

Methods for isolation and purification of recombinant proteins are described. Fusion proteins incorporating a cleavage site sensitive to proteolysis by a plant virus proteinase may be cleaved from carrier proteins to provide high yields of protein product. Methods employing a plant virus proteinase to cleave expressed fusion proteins are particularly suitable for obtaining proteolytically sensitive polypeptides in the presence of added cell protease inhibitors. Also disclosed are recombinant vectors useful for overproducing plant virus proteinases in a suitable host.

20 Claims, 13 Drawing Sheets

```
GGAGAAAGCT TGTTTAAGGG ACCACGTGAT TACAACCCGA TATCGAGCAC CATTTGTCAT
TTGACGAATG AATCTGATGG GCACACAACA TCGTTGTATG GTATTGGATT TGGTCCCTTC
ATCATTACAA ACAAGCACTT GTTTAGAAGA AATAATGGAA CACTGTTGGT CCAATCACTA
CATGGTGTAT TCAAGGTCAA GAACACCACG ACTTTGCAAC AACACCTCAT TGATGGGAGG
GACATGATAA TTATTCGCAT GCCTAAGGAT TTCCCACCAT TTCCTCAAAA GCTGAAATTT
AGAGAGCCAC AAAGGGAAGA GCGCATATGT CTTGTGACAA CCAACTTCCA AACTAAGAGC
ATGTCTAGCA TGGTGTCAGA CACTAGTTGC ACATTCCCTT CATCTGATGG CATATTCTGG
AAGCATTGGA TTCAAACCAA GGATGGGCAG TGTGGCAGTC CATTAGTATC AACTAGAGAT
GGGTTCATTG TTGGTATACA CTCAGCATCG AATTTCACCA ACACAAACAA TTATTTCACA
AGCGTGCCGA AAAACTTCAT GGAATTGTTG ACAAATCAGG AGGCGCAGCA GTGGGTTAGT
GGTTGGCGAT TAAATGCTGA CTCAGTATTG TGGGGGGCC ATAAAGTTTT CATGAGCAAA
CCTGAAGAGC CTTTTCAGCC AGTTAAGGAA GCGACTCAAC TCATGAATGA ATTGGTGTAC
TCGCAA
```

FIG. 1

Sequence of TEV CS and Cloning Sites

```
          EheI      NcoI   BamHI        SmaI      EcoRI
GAG AAT CTT TAT TTT CAG GGC GCC ATG GAT CCC GGG CGA ATT C
 E   N   L   Y   F   Q   G   A   M   D   P   G
                         ↑
                    Peptide bond cleaved
     Proteinase recognition
         Sequence
```

METHOD OF ISOLATION AND PURIFICATION OF FUSION POLYPEPTIDES

The United States Government has certain rights in the present invention in accordance with grant GM 04700 awarded by the National Institutes of Health.

BACKGROUND OF THE INVENTION

1. Field of the Invention

The invention relates generally to the field of molecular biology and to methods of isolating and purifying recombinant proteins. The invention also includes DNA constructs engineered to include DNA encoding a desired polypeptide and a unique plant virus proteinase recognition site. Expression vectors for use in overproducing recombinant plant virus proteinase, particularly tobacco etch virus proteinase, are also part of the invention. The recombinant plant virus proteinase is unaffected by cell protease inhibitors, thereby permitting isolation of significantly improved yields of proteolytically sensitive polypeptides in the presence of added cell protease inhibitors. Methods of overproducing plant viral proteinases are also disclosed.

2. Description of Related Art

Isolation and purification of recombinant polypeptides expressed in bacterial and other hosts is of interest because these systems are capable of providing relatively large quantities of polypeptides having therapeutic or commercial value. Such systems are especially desirable where synthesis is expensive and time-consuming and/or the protein occurs naturally only in small quantities. Unfortunately, yields of recombinant polypeptides are frequently drastically reduced because of any one of several problems that may be encountered, including difficulties associated with isolation, purification and segregation.

Fusion proteins are frequently the method of choice for purifying proteins because of the benefit of allowing affinity purification and the increase in solubility that is frequently observed. There are, however, several disadvantages associated with release of the protein of interest from the carrier protein. The proteases employed for cleavage, typically thrombin and factor x, have recognition sites with low specificity so that the protein is often cleaved at several sites. Cleavage may result in several foreign amino acid residues attached to the protein, thereby altering the properties of the protein.

Several proteases not only lack selectively but are also relatively inefficient, so that yields of the cleaved protein are significantly decreased. In some cases, this is due to impurities which may either partially inactivate the protease or, more commonly, themselves have nonselective proteolytic activity.

A selective tobacco etch virus proteinase cleavage site said to be useful for expressing fusion proteins has been disclosed (Jarvis and Carrington, 1993). Unfortunately, specific constructs disclosed were stated to be useful only for expression in insect cells.

Fusion proteins tend to be more soluble than the single protein, contributing to higher yields and simpler purification; however, there are often problems in removing the fusion "partner". This is generally accomplished by cleaving the two proteins, provided there is a selective cleavage site that will leave the desired protein intact. Often, however, it is difficult to obtain the desired polypeptide free of contaminating segments of the fusion partner.

Numerous recombinant systems are available for promoting synthesis of fusion proteins in a bacterial host cell. Such fusion proteins may be generated as single chain polypeptides following translation of appropriately joined DNA segments. Fusion proteins incorporate the protein of interest, a carrier protein and, typically, a polylinker sequence between the two proteins. Carrier proteins may be selected on the basis of transport characteristics to assure that the fusion protein is secreted into either the periplasmic space or the growth medium on the basis of solubility. Regardless of the amount of fusion protein expressed, isolation and purification of the desired polypeptide is frequently difficult and inefficient.

One approach to the isolation problem has been to engineer fusions of a desired polypeptide with a carrier protein having specific binding properties; for example, binding to affinity columns that incorporate antibodies, chelates, metals etc. Isolation is thereby facilitated and product yields improved. Recombinant eukaryotic proteins have been synthesized from gene fusions of foreign proteins with the carbohydrate-recognition domain (CRD) of the galactose-specific rat hepatic lectin (Taylor and Drickamer, 1991). These fusion proteins are isolated affinity chromatography, then cleaved at a proteinase-sensitive linker.

A popular carrier protein is *Staphylococcus aureus* protein A. A recombinant protein is first isolated by affinity chromatography, which binds protein A, then separated by domain-specific enzymatic cleavage with chymotrypsin while immobilized on the affinity column. The affinity column is specific for protein A which binds to the $F_c$ portion of certain subclasses of human immunoglobulins, including IgG. A detailed description of the use of protein A in this manner is provided in International Patent Application Number WO 84/03103 incorporated herein by reference.

Several proteins have been isolated and purified using this general scheme, including DNA-binding domain of the glucocorticoid receptor (Dahlman, et al., 1989). Eukaryotic proteins expressed in *Escherichia coli* have been isolated from crude bacterial extracts by affinity chromatography on glutathione agarose when the protein is expressed as a polypeptide in frame with glutathione-S-transferase (Smith and Johnson, 1988). The vector system usually incorporates specific protease cleavage sites to facilitate proteolysis for cleavage of the desired protein from glutathione-S-transferase. Modification of the vector in one instance to include a glycine-rich linker has resulted in increased thrombin cleavage efficiency for several fusion proteins (Guan and Dixon, 1991).

Despite improved yields and facilitated purification when employing these carrier "affinity" protein fusions, expressed fusion proteins are frequently seriously damaged or even destroyed by endogenous bacterial proteases. Yields are therefore low despite an efficient expression vector. This is particularly a problem for protease sensitive small proteins or peptides. Addition of cell protease inhibitors to crude bacterial extracts may alleviate proteolysis; however, cleavage of a foreign protein from its carrier protein becomes a problem because the inhibitors will typically inactivate added cleavage proteases that are commonly employed for this purpose. The presence of added proteases and protease inhibitors also complicates purification because of additional species and product dilution.

As previously mentioned, a significant problem may be cleavage of the expressed foreign protein or peptide by the proteinase employed (e.g., thrombin, factor x), employed to release the desired polypeptide from the carrier protein.

These spurious cleavages are the result of the limited specificity displayed by the proteinases frequently employed.

Finally, in the isolation of recombinant proteins, spurious amino acids are frequently attached to the cleaved polypeptide product. These amino acids are typically present when a linker is cleaved, and the unrelated amino acids may have an effect on the properties of the isolated protein. This may be critical for proteins produced for human therapeutics. Ideally, one seeks efficient cleavage to produce pure native protein free of extraneous amino acid short sequences or residues.

SUMMARY OF THE INVENTION

The present invention addresses one or more of the foregoing problems by providing methods of producing high yields of recombinant proteins. The new methods employ a unique plant virus proteinase recognition site incorporated into the recombinant protein. Cleavage of this unique cleavage site employing recombinant plant viral proteinase is efficient and specific, even in the presence of cell protease inhibitors. The cleavage leaves only an extra glycine residue. Additionally, recombinant plant virus proteinase may be overproduced in eukaryotic or prokaryotic cells and purified to near homogeneity. Without contaminating proteases, the plant viral proteinase preparations are superior to most other proteinases commonly employed because of specificity resulting in increased yields of intact protein.

The recombinant plant viral proteinases or any desired fusion proteins may be prepared with "tags". These tags, such as affinity tags, allow binding of the expressed fusion product to a carrier, isolation from other cell material, and cleavage in a simple, rapid operation. Yields of desired polypeptides are significantly increased due to efficient and substantially complete cleavage by the viral proteinase. Resistance of the recombinant plant virus proteinase to cell protease inhibitors which may be added to cell extracts to prevent cleavage by endogenous cell proteases also is a factor in increasing yields.

As used herein, it is not intended that the terms protein, peptide and polypeptide should necessarily indicate a limit on the size of the polymer. Peptides are generally relatively short sequences, on the order of up to 50 or so amino acids, while polypeptides and proteins are typically longer, although the terms peptide, protein and polypeptide may be used interchangeably in the context of the present invention.

A general object of the invention is to produce recombinant proteins in a suitable host thus providing readily isolated and purified fusion products. The novel methods herein disclosed are especially suitable for proteolytically sensitive proteins whose yields are decreased due to the presence of cell proteases in the host organism. Generally, the method involves DNA transformation of a suitable host. The DNA includes one DNA segment encoding a virus proteinase cleavage site and another DNA segment encoding the protein or polypeptide that one desires to isolate. The host is transformed with the DNA, then cultured to promote transcription and translation of the DNA. Recombinant protein is collected after cleaving at the virus proteinase cleavage site with a virus proteinase. Generally this will be the corresponding virus from which the cleavage site was constructed.

Cell extract may be prepared or incubated in the presence of cell protease inhibitors. The plant virus cleavage site is not susceptible to proteolysis by ordinary cell proteases. The plant virus proteinase itself is unaffected by ordinary protease inhibitors so that such inhibitors may be added in amounts sufficient to inactivate cell proteases. Typical and commonly used cell protease inhibitors include leupeptin, pepstatin A, PMSF, E-64, TLCK, bestatin and aprotinin. However, the inventors believe that any of a number of proteinase inhibitors may be employed so long as they are not inhibitors of the proteinase used to release a foreign protein from the carrier protein. The practitioner will typically culture in a media or grow in an environment suitable for the host selected, prepare cell extract, then add appropriate cell protease inhibitors. The desired protein may be purified using standard procedures such as chromatography, electrophoresis or density gradient centrifugation.

In preferred embodiments, DNA encoding the virus proteinase cleavage site will include a nucleic acid segment coding for a carrier protein or fusion partner, i.e., a protein fused with the protein of interest where the carrier has properties that facilitate its isolation from other proteins. Examples of carrier proteins are not limited to any particular protein, but may be selected from a wide variety of proteins such as beta galactosidase, ubiquitin, glutathione S-transferase, alkaline phosphatase, maltose binding protein, Protein A, polyhistidines, monoclonal antibody epitopes and so forth. Carrier proteins typically will be selected on the basis of characteristics contributing to easy isolation, most desirable being those that are readily secreted by the microorganisms or which have some property or feature which facilitates isolation and purification of the protein. Glutathione S-transferase, maltose binding protein and polyhistidine sequences, for example, are generally preferred because there are readily available affinity columns to which they can be bound and eluted. Other suitable fusion partners include antigenic tags that readily bind to corresponding antibodies or proteins that have special affinity properties, for example, selective binding to particular metals, as with polyhistidine peptide binding to nickel.

In one aspect, the present invention relates to expression and overproduction of recombinant virus proteinase. Sources of virus proteinase include flavi-, picorna- and potyviruses. The method is considered particularly suited for overproducing potyvirus proteinases in E. coli or yeast cells and is most preferred for tobacco etch virus (TEV). In this regard, the inventors are the first to have overproduced recombinant tobacco etch virus proteinase in E. coli or yeast cells. The recombinant TEV proteinase, unlike the proteinase obtained from natural sources, is pure, free of extraneous proteins and other contaminants and, surprisingly, has been found by the inventors to be highly resistant to the action of commonly employed cell protease inhibitors such as leupeptin and the like.

Also included as part of the present invention are engineered or recombinant host cells transformed by the aforedescribed DNA. As used herein, the term "engineered" or "recombinant" cell is intended to refer to a cell into which a recombinant gene, such as a gene encoding a viral proteinase unit has been introduced. Therefore, engineered cells are distinguishable from naturally occurring cells. Engineered cells are those cells having a gene or genes introduced through the hand of man. Recombinantly introduced genes will either be in the form of a cDNA (i.e., they will not contain introns), a copy of a genomic gene, or will include genes positioned adjacent to a promoter not naturally associated with the particular introduced gene.

Generally speaking, it may be more convenient to employ as the recombinant gene a cDNA version of the gene. It is believed that the use of the cDNA version provides advantages and that the size of the gene will generally be much smaller and more readily employed to transfect a target than will be a genomic gene, which will typically be up to an order of magnitude larger than the cDNA gene. However, the inventors do not exclude the possibility of employing a genomic version of a particular gene in the appropriate host.

Numerous host cells may be selected as appropriate for transformation and expression of the described fusion proteins, including mammalian, insect, fungal, plant and bacterial host cells which are particularly desirable. Commonly used bacterial strains include Escherichia, Klebsiella, Erwinia, Bacillus, Staphylococcus and Salmonella. *E. coli* TG-1, or *E. coli* BL-21 are considered to be preferred bacterial strains. Eukaryotic cells such as *Saccharomyces cerevisiae* or transgenic plants may also be employed with good results.

The recombinant DNA of the present invention may be used either in the form of an expression vector or as the DNA alone to transform a host cell. Methods of injecting DNA directly into a cell are known, such as by electroporation, biolistic techniques or transformation. Alternatively, vectors incorporating the DNA may be prepared, for example, by packaging in vitro into bacteriophage as found in Maniatis, et al. (1982). Cells are then infected with the recombinant phage, plated and grown in appropriate media.

Vectors employed in prokaryotic systems will include an origin of replication, a promoter and transcriptional termination signal and preferably a selective marker. Examples of promoters include tac, T7, trc, trp, or $P_L$. Some promoters such as Ptac or Ptrc, when present in *E. coli* host cells, are repressed by lac repressor. Expression of the recombinant protein encoded in the vector may be induced with IPTG. Other inducible promoters include Pmal and the aforementioned trp and $P_L$. This feature is useful for expression of toxic proteins because one may increase cell density in the culture prior to inducing expression of the desired polypeptide.

Regarding eukaryotic cells, it is believed that numerous eukaryotic expression vectors could be utilized for the expression of fusion proteins that incorporate viral proteinase cleavage sites, whether wild type or mutant; for example, Baculovirus-based, glutamine synthetase-based, neomycin phosphotransferase or dihydrofolate reductase-based systems could be employed. Plasmid vectors incorporating an origin of replication and an efficient eukaryotic promoter, as exemplified by the eukaryotic vectors of the PCNV series, such as PCNV-5, may also be of use.

For expression in this manner, one would position the coding sequences adjacent to and under the control of the promoter. It is understood in the art that to bring the coding sequence under the control of such promoter, one positions the 5' end of the transcription initiation site of the transcriptional reading frame of the protein between about 1 and 50 nucleotides "downstream" of (i.e. 3' of) the chosen promoter.

In such eukaryotic systems, one would also typically desire to incorporate into the transcriptional unit which includes the viral proteinase cleavage site, an appropriate adenylation site (e.g., 5' AATAAA-3') if one was not contained with the original clone segment. Typically, the poly A addition site is placed about 30 to 2000 nucleotides "downstream" of the termination site of the protein at a position adjacent to a transcription termination signal.

The virus proteinase cleavage site which is included in the recombinant DNA of the present invention will generally be selected from naturally occurring cleavage sites of a virus proteinase. The proteinase cleavage site will typically be unique and susceptible to cleavage only by the proteinase. Of course the amino acid sequence of the cleavage site will depend on the particular viral proteinase one desires to use to cleave the fusion protein. It is believed that different potyviral proteinases will have unique cleavage sites responsive only to the viral proteinase from which it is derived. Thus it may be expected that some cleavage sites will be more selective than others or may be more desirable for use in certain host cells.

The inventors have discovered that tobacco etch virus $NI_a$ proteinase cleavage sites are particularly suited for DNA constructs employed to transform bacterial hosts. Tobacco etch virus $NI_a$ proteinase cleavage sites are encoded within the TEV nucleic acid sequence shown in FIG. 1. As a practical matter, a 7-amino acid (7-mer) sequence will permit effective cleavage, although there is no reason why longer segments including these residues could not be used. The cleavage sequence will generally include either a glutamine-glycine or a glutamine-serine dipeptide, between which cleavage occurs. Residues other than gly or ser may be used. Mutagenesis studies have shown that a number of amino acids are functional in this position, although protein degradation will be a factor and higher yields may be obtained using residues which are stable when viewed in the context of N-terminal rules of Varshausky (Bachmain, et al., 1986).

Preferred examples of tobacco etch virus recognition sequences include a 7-mer sequence represented by glu xaa xaa tyr xaa gln ser (SEQ ID NO:1) or glu xaa xaa tyr xaa gln gly (SEQ ID NO: 2) where xaa represents Asn (P6), Leu (P5) or Phe (P2). A particularly preferred sequence is glu asn leu tyr phe gln gly (SEQ ID NO:3).

The viral proteinases employed in the practice of the invention are resistant to the usual cell protease inhibitors. Such resistance allows one to use relatively large quantities of cell protease inhibitors when isolating polypeptide fusion products. The inventors have found, for example, that cell protease inhibitors such as leupeptin, pepstatin A, phenylmethylsufonyl fluoride (PMSF), ethylenediamine tetraacetic acid (EDTA), N-α-p-tosyl-L-lysine chloromethyl Ketone (TLCK) or aprotinin may be used during isolation without affecting the activity of viral proteinase. In preferred embodiments, TEV proteinase is added to cell lysate and will effectively cleave the fusion protein in the presence of added cell protease inhibitors.

It is contemplated that several types of viral proteinases may be utilized and will provide a wide array of cleavage specificities. Most potyvirus cleavage sites have not been well characterized and each potyvirus $NI_a$ proteinase appears to be slightly different. The inventors believe that certain individual viral proteinases may not process other potyvirus substrates (Parks and dougherty, 1991). Other proteinases such as picorna and flavi viruses are expected to have reduced substrate specificity compared with TEV proteinase.

BRIEF DESCRIPTION OF THE DRAWINGS

FIG. 1 shows the DNA nucleotide sequence for the 27k tobacco etch virus (TEV) $NI_a$ proteinase (SEQ ID NO:4). This sequence is represented by base pairs numbered 6256 through 6981 of the full TEV gene sequence (Allison, et al., 1986, incorporated herein by reference).

FIG. 7 shows the construction of the plasmids employed to generate pGEX-CS3 shown in FIG. 8.

DETAILED DESCRIPTION OF PREFERRED EMBODIMENT

The present invention includes improved methods of purifying recombinant polypeptides in transformed cells. In general, the methods take advantage of a unique cleavage site obtained from a plant virus proteinase and the relative insensitivity of the virus proteinase to commonly available protease inhibitors which are desirably added to cell extracts to prevent proteolysis of the recombinant protein. In a particular example, a functional cleavage site for tobacco etch virus (TEV) proteinase is incorporated into the polylinker region of a convenient cloning vector, enabling isolation of fusion polypeptides in the presence of relatively large amounts of added cell protease inhibitors. Yields of polypeptides sensitive to cell proteases are thus significantly increased. Isolation of a desired polypeptide is more efficient because cleavage is selective for the unique potyvirus proteinase site. Engineered fusion proteins linked to various carriers or fusion partners designed for selective absorption may be efficiently separated from cellular debris and other protein contaminants prior to cleaving the polypeptide from the carrier with the plant virus proteinase to release the polypeptide from the carrier.

Figure 8:
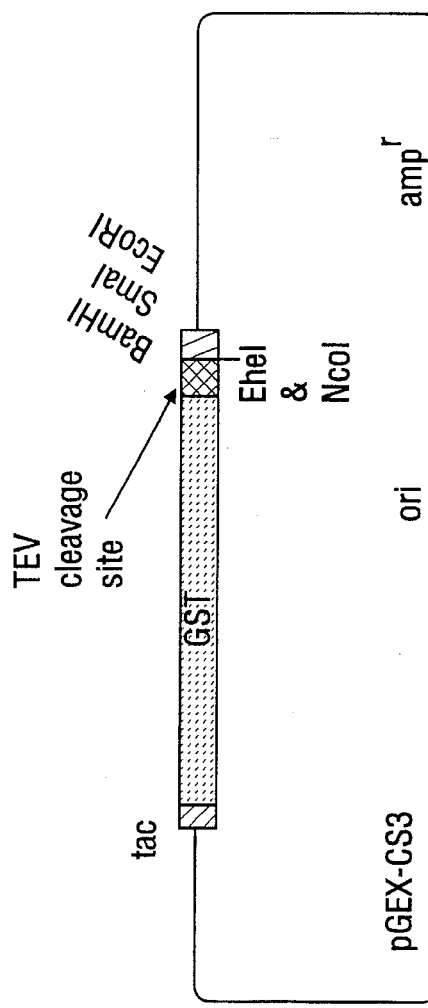
FIG. 8 shows the construction of a modified pGEX expression vector, pGEX-CS3. The sequences shown below the plasmid indicate restriction endonuclease cloning sites and the cleavage site sensitive to TEV proteinase. The nucleotide sequence is represented by SEQ ID NO:5 and the amino acid sequence is represented by SEQ ID NO:6.
Figure 9:
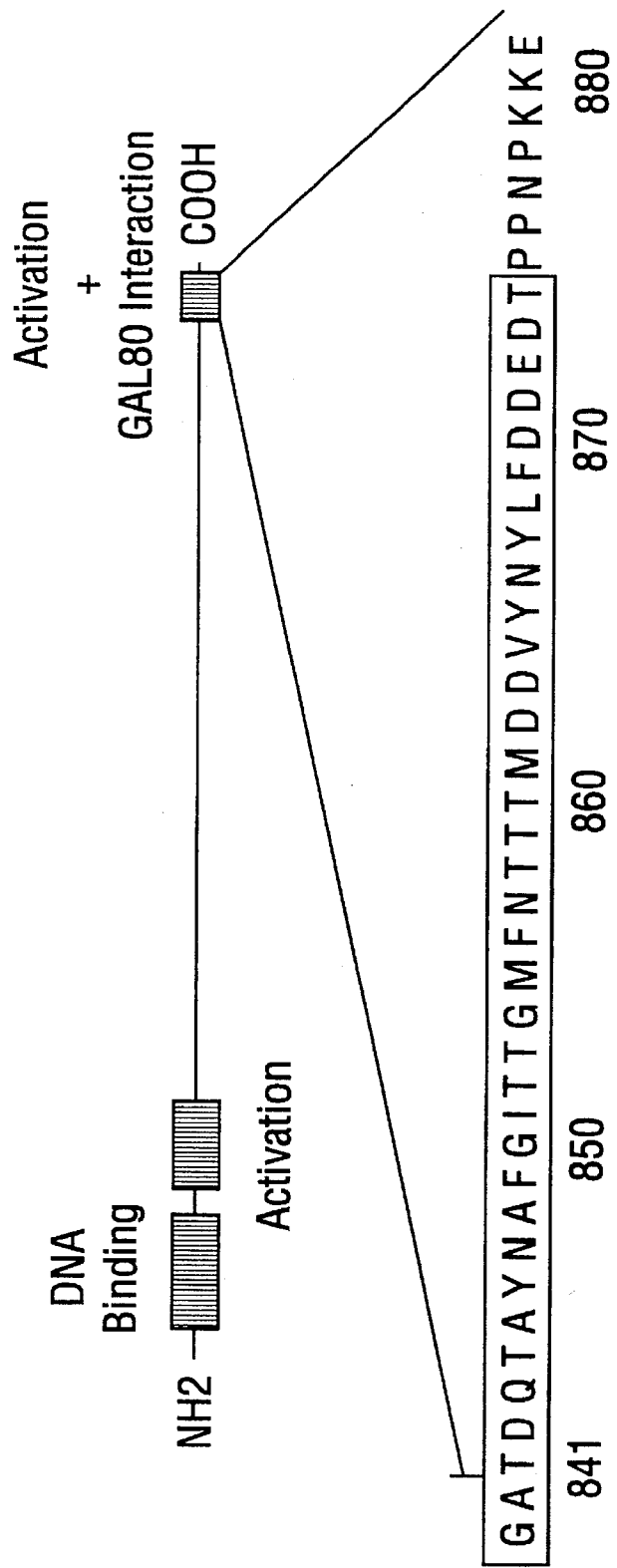
FIG. 9 shows the sequence of the 34-mer of GAL4 which was expressed in E. coli as a fusion protein to glutathione S-transferase (residues 3 through 36 of SEQ ID NO:7).

Expression vectors incorporating DNA encoding unique potyvirus cleavage sites may be constructed employing well known recombinant techniques. FIG. 8 indicates how vector pGEX is modified by the introduction of a primer-introduced cleavage site. In this construct with glutathione-S-transferase as the fusion protein, a 33 bp DNA coding sequence GAG AAT CTT TAT TTT CAG GGC GCC ATG GAT CCC (residues 1–33 of SEQ ID NO:5) encodes the 11-mer peptide sequence glu asn leu tyr phe gln gly ala met asp pro (residues 1–11 of SEQ ID NO:6). This construct contains two restriction sites for EheI and NcoI. DNA may be cloned into either site maintaining the reading frame of the inserted DNA.

Figure 11A:
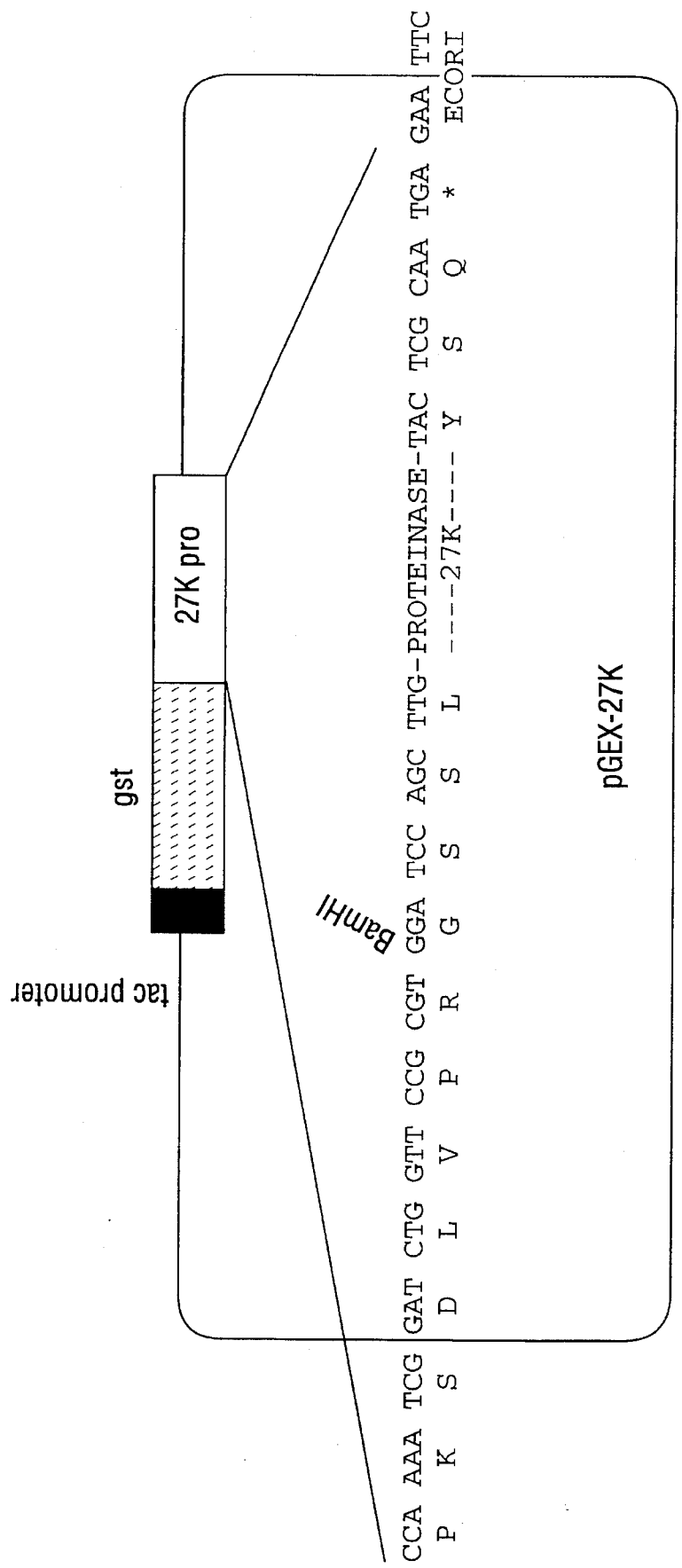
FIG. 11 presents schematic drawings of plasmids used in the expression of the TEV $NI_a$ proteinase: Panel A is plasmid pGEX-27k; panel B is pGex-6Hispro; and panel C is pTRC-7Hispro. Sequences shown below represent the nucleotide and amino acid sequences surrounding the fusion proteins. In panel A, the first nucleotide sequence is SEQ ID NO:12, the second nucleotide sequence is SEQ ID NO:13, and the amino acid sequence is SEQ ID NO:14. In panel B, the first nucleotide sequence is SEQ ID NO:15, the second nucleotide sequence is SEQ ID NO:13, and the amino acid sequence is SEQ ID NO:16. In panel C, the first nucleotide sequence is SEQ ID NO:17, the second nucleotide sequence is SEQ ID NO:18, the first amino acid sequence is SEQ ID NO:19, and the second amino acid sequence is SEQ ID NO:20.
Figure 11B:
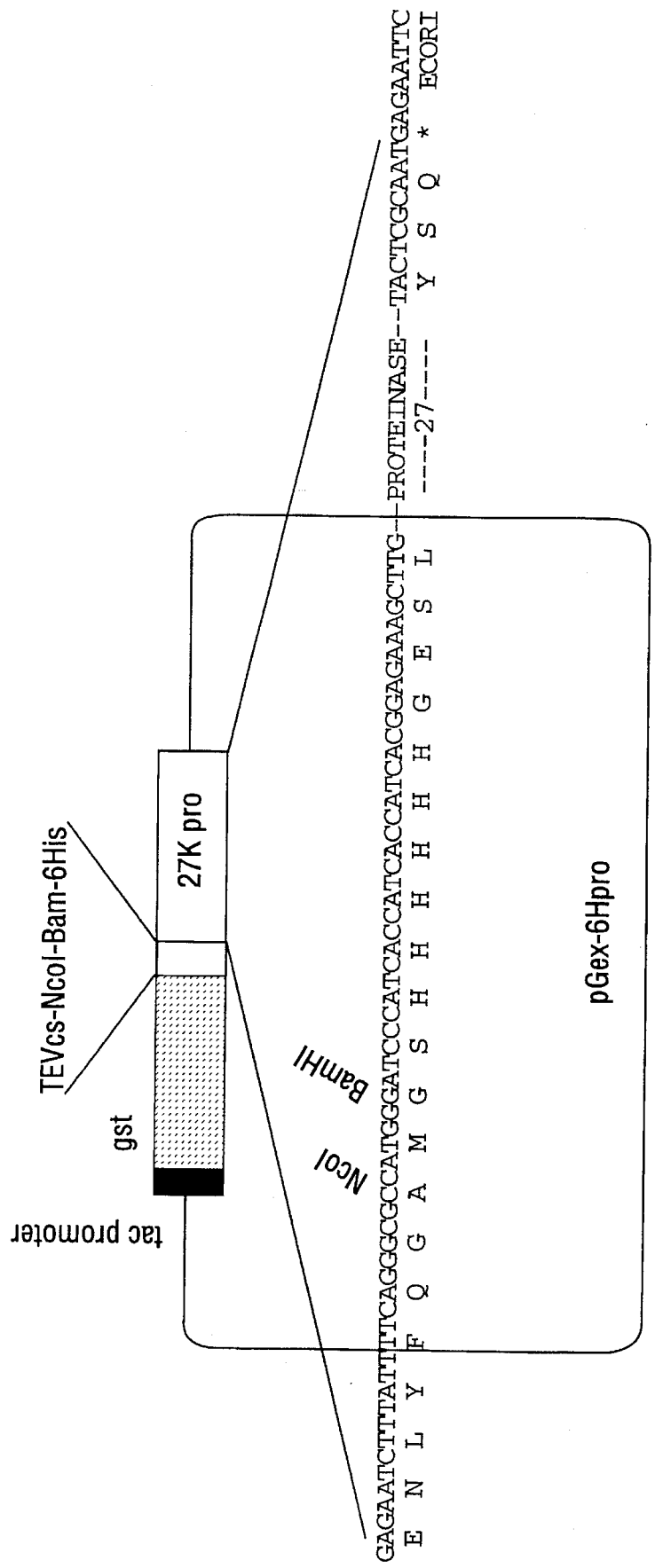
Figure 11C:
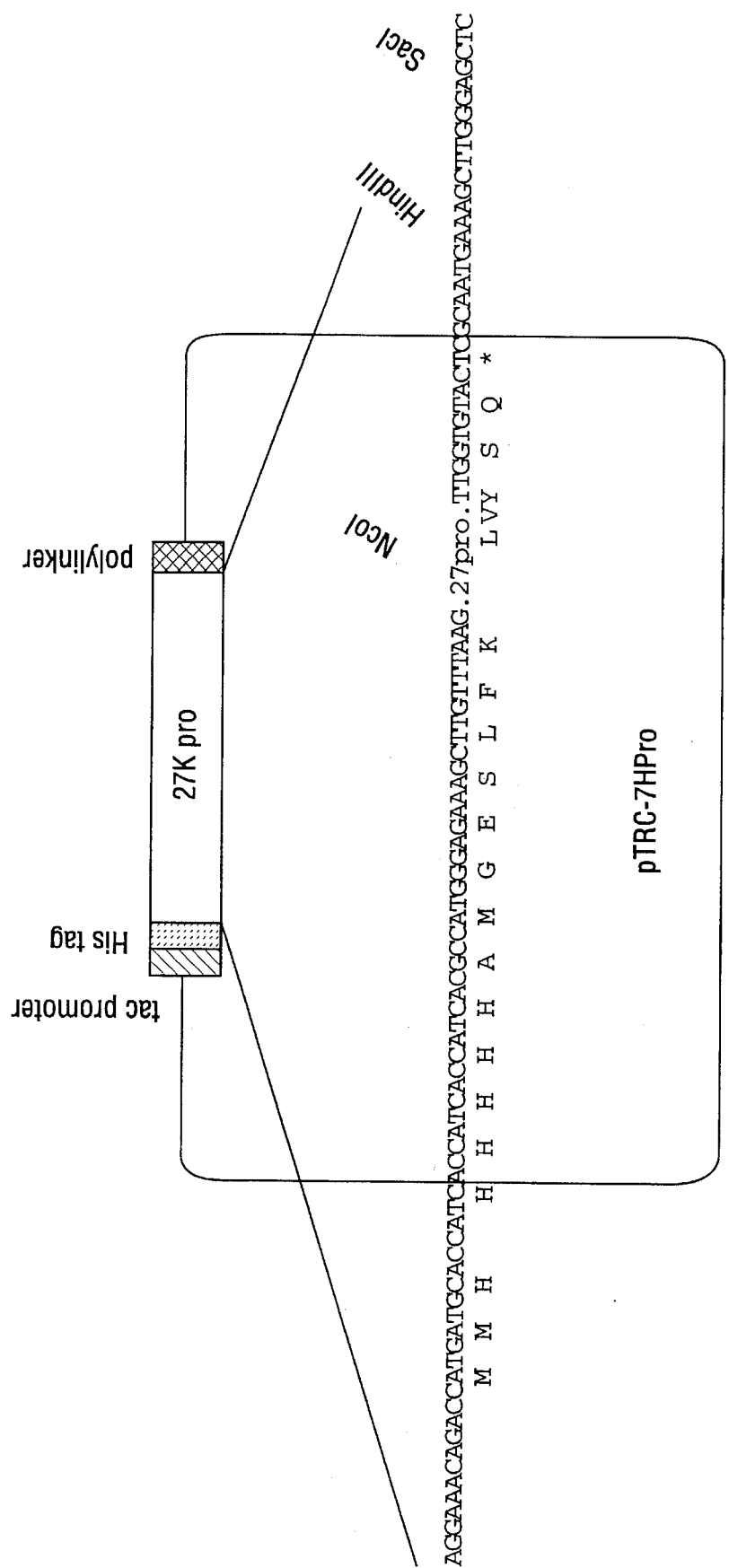

In one embodiment, the invention includes expression vectors appropriately constructed for expression in various hosts. Plasmid vectors containing the tobacco-etch virus (TEV) $NI_a$ proteinase coding sequence were linked to a sequence which codes for a polyhistidine tract. In appropriately transformed host cells, the product is expressed as TEV proteinase with polyhistidine end residues. The polyhistidine tract may be placed at the amino or carboxyl terminus of the 27k $NI_a$ proteinase. A typical tag contains six histidine residues. In an exemplary embodiment, one employs pN-27, a readily available plasmid containing the TEV-27 kDa proteinase sequence. The 27 kDa $NI_a$ gene of TEV is amplified by PCR in a manner such that an NcoI site and Bam-HI site followed by codons for a polyhistidine tract are added at the 5' end. The 27 kDa gene for the TEV $NI_a$ proteinase may then be inserted into plasmid pGEX-CS which is constructed with a glutathione S-transferase gene and a tac promoter. The resulting plasmid is designated pGEX-6HisPro. The proteinase initially expressed from this system is a fusion protein containing N-terminus glutathione S-transferase, a tobacco etch virus CS, a 6-histidine residue, and the 27k $NI_a$ proteinase C-terminus. This 56–58 kDa fusion protein undergoes self-cleavage to generate a GST moiety (26 kDa) and a his-tagged proteinase moiety (29 kDa). This plasmid coding for this fusion is presented in a schematic form in FIG. 11.

In yet another embodiment one again employs plasmid pN-27. Appropriately designed primers are used to amplify the 27 kDa sequence to generate a DNA coding for a 27 kDa proteinase fused with a polyhistidine sequence. This DNA is cut with BspHI at the 5' end and with Sac-1 at the 3' end and ligated into pTRC-99a previously digested with Nco-1 and Sac-1 (Pharmacia). The resulting plasmid is pTRC-7-His pro. This plasmid is transcribed and translated in a suitably transformed host cell to provide a 29 kDa TEV NI$_a$ proteinase. The 27 kDa NI$_a$ proteinase derived from this plasmid is fused at the N-terminal with a polyhistidine tract sequence which has a methionine residue at the N-terminus. At least 5 mg per liter of active proteinase of greater than 95% purity is typically obtained.

Bacterial cells are conveniently employed for transformation and expression of recombinant proteins although eukaryotic cells may be preferred for certain proteins. The expression vector shown in FIG. 8 was constructed by cloning a segment of TEV containing the proteinase recognition site into the pGEX polycloning site.

Once transformed, E. coli cells are grown and harvested as described in detail in Example 1. When using this system, the lac repressor (product of the lacI gene) binds to the P$_{lac}$ promoter, repressing expression of GST/fusion protein. Upon induction with IPTG, derepression occurs and the GST fusion protein/polypeptide is expressed. At harvesting, leupeptin, pepstatin and other protease inhibitors are added. The fusion protein product is separated from other cell proteins, most conveniently by affinity chromatography. TEV proteinase is then employed to cleave the protein from its affinity carrier. By design, the cleaved protein carries only one or a few extra amino acids at the amino terminus.

E. coli strains TG1 and LB21 are well-known and are described in the Molecular Cloning Manual by Sambrook, Fritsch and Maniatis, Appendix 9, Cold Spring Harbor Press, 1989. A source for TG1 is Amersham Corporation (Arlington Heights, Ill. 60065. A source for BL21 is New England Biolabs (Beverly, Mass. 01915).

EXAMPLE 1

One of the problems in exploiting plant virus proteinases is their lack of availability in a purified active form. Potyvirus proteinases such as tobacco etch virus NI$_a$ proteinase are difficult to isolate and purify to homogeneity in an active form. The present invention is a method of overproducing such viral proteinases in bacterial cells, illustrated with three different constructs for expression of tobacco etch virus proteinase.

Expression and Purification of Glutathione S-Transferase/27 kDa Tobacco Etch Virus Proteinase Using PCR amplification, the 27k gene encoding TEV proteinase (SEQ ID NO:4) was obtained from plasmid pN-27, the 5' primer having NcoI and Bam restriction sites and the 3' primer having an EcoRI site. The DNA sequence encoding 27k TEV proteinase and the restriction sites was inserted into pGEX-2T, shown schematically in FIG. 11, which contained the glutathione-S-transferase coding sequence. This resulting plasmid designated pGEX-2T/27k coded for a 56 kDa fusion protein containing GST at the amino terminus and the TEV 27k at the carboxy terminus (FIG. 11).

Construction of Expression Vector for Purification of Glutathione S-Transferase-Tagged TEV Proteinase The plasmid which carries a gene for ampicillin resistance was transformed into E. coli TG1 and/or BL21 cells. In some cases the bacteria also contained an additional plasmid, plysS, coding for chloramphenicol resistance and the production of lysozyme which aided in cell disruption.

Plasmid pGEX-CS3

Plasmid pGEX-CS3 was constructed starting with plasmid pGEX-1 obtained from Pharmacia. A TEV cleavage site was added to the carboxy terminus of the glutathione S-transferase gene using a polymerase chain reaction amplification and 2 oligonucleotide primers. The primer sequences were 5' G TGG ATC CAT GGC GCC CTG AAA ATA AAG ATT CTC GAG ATG (SEQ ID NO:8) for the 3' primer and 5' TA TCC ATG GCC CCT ATA CTA GG-3' (SEQ ID NO:9) for the 5' primer. These two oligonucleotide primers resulted in a DNA fragment that coded for the following: NcoI restriction endonuclease site, glutathione S-transferase, a TEV cleavage site sequence (glu asn leu tyr phe gln; SEQ ID NO:10) and the nucleotide sequence which codes for the overlapping restriction endonuclease recognition sites EheI, NcoI and BamHI.

Figure 7A:
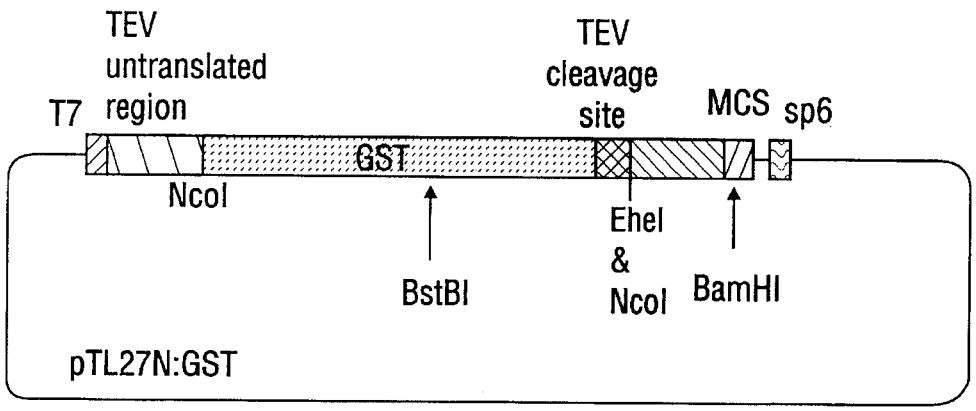
FIG. 7A is pTL27N:GST which was created from pTL27N.
Figure 7B:
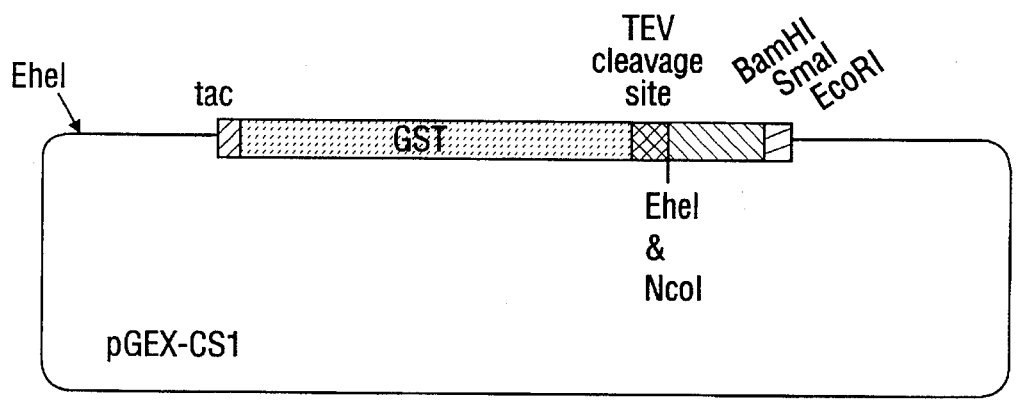
FIG. 7B shows the general construction of pGEX-CS1 resulting from ligation of pTL27N:GST with pGEX-1 (Pharmacia).
Figure 7C:
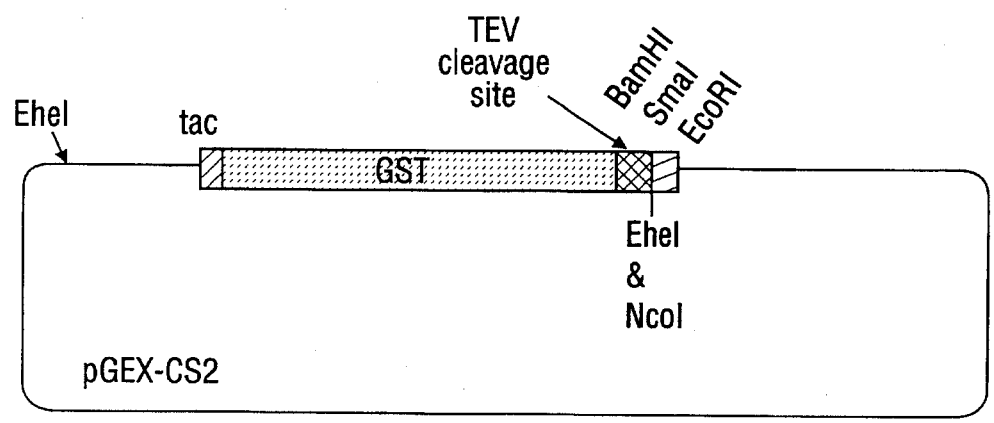
FIG. 7C shows pGEX-CS-2 which was a modification of pGEX-CS-1.

The amplified DNA fragment was digested with NcoI and ligated into an expression vector designated pTL27N (Parks, et al., 1992). This intermediate vector was designated pTL27N:GST (FIG. 7A). This vector was digested with BstBI and BamHI and the resulting fragment containing part of the GST ORF with TEV cleavage site was isolated and ligated into pGEX-1 which had been digested with BstBI and BamHI. The resulting plasmid was designated pGEX-CS1 (FIG. 7B). Sequences downstream of the TEV cleavage site sequence were eliminated by digesting the plasmid with NcoI and BamHI, ends were filled in with Klenow polymerase and the plasmid was re-ligated. The resulting plasmid was designated pGEX-CS2 (FIG. 7C). This plasmid was modified by a partial NarI digestion, filling the ends with Klenow and religating the plasmid. This eliminated a second EheI site that was part of the pGEX-1 plasmid. The new plasmid was designated pGEX-CS3 (FIG. 8) and could be used to express a variety of proteins or peptides by taking advantage of convenient restriction sites indicated in FIG. 8.

Plasmid pGEX-27K Pro

A fragment containing the 27 kDa TEV proteinase was amplified by PCR from plasmid pTL27/5473 with primers that introduced BamHI and EcoRI sites at the 5' and 3' ends of the gene respectively. pTL27/58 is an in vitro expression vector cDNA of TEV genomic RNA. The plasmid is described in Parks, et al., 1992. The resulting ~750 bp PCR fragment of the TEV protease was cut with BamHI and EcoRI and cloned into the BamHI and EcoRI sites of pGEX-2T (Pharmacia LKB, Gaithersburg, Md.). The resulting plasmid, pGEX-27k TEV Proteinase, yields a GST-TEV Protease fusion protein upon induction with IPTG.

Plasmid pGEX-6HisPro pGEX-6HisPro was constructed by polymerase chain reaction amplification of the 27 kDa TEV ORF with oligonucleotide primers which added an NcoI restriction endonuclease site and codons for 6 additional histidine residues to the amino terminus, and a stop codon and recognition sequence for EcoRI at the carboxy terminus. This resulting DNA fragment was digested with the restriction enzymes NcoI and EcoRI and ligated into plasmid pGEX-CS1 also digested with NcoI and EcoRI. Translation of this pGEX-6His-Pro sequence resulted in a protein product that was translated initially as a ~52 kDa precursor which underwent self-cleavage to generate glutathione S-transferase (GST)

and the TEV 27 kDa proteinase subunit with a methionine and 6 histidines at the N-terminus.

Plasmid pTRC-7His-Pro

Another proteinase expression plasmid, pTRC-7His-Pro, was generated by polymerase chain reaction amplification using oligonucleotide primers which generated a nucleotide sequence containing a BspHI endonuclease restriction site, 7 His codons and an NcoI restriction site at the amino terminus of the proteinase ORF. A second oligonucleotide primer added a stop codon and HindIII and SacI restriction endonuclease sites at the carboxy terminus of the 27 kDa ORF. This DNA fragment was amplified, digested with the restriction enzymes BspHI and SacI and the fragment was ligated into pTRC99A (Pharmacia), digested with restriction enzymes NcoI and SacI. Proteinase expressed from this plasmid had an additional met residue and 7 his residues at the N-terminus.

Induction of Protein Expression Using pGST/27K

Transformed *E. coli* TG1 cells were inoculated into L-broth and grown overnight at 37° C. The culture was diluted 1:10 into L-broth containing ampicillin and chloramphenicol at a final concentration each of 25 µg/ml. When grown in a fermenter, 1:100 dilutions were employed. Cultures were grown to $OD_{600\,nm}$ ~0.6, or to $OD_{600}$ nm =3–4 if grown in a fermenter. After removing a culture sample as a control, the remaining culture was induced by adding IPTG to a concentration of 0.3 mM. Culturing was continued for an additional 2–4 hours and the cells were then harvested by centrifuging at 5000×g. Cells were resuspended in 1:100 PBS, pH 7.3 containing 1 mM PMSF, 1 µg/ml leupeptin, 1 µg/ml pepstatin A, 1 mM DTT or 0.2 mM sodium sulfite and 0.5 mM EDTA.

Cells were lysed by freeze thawing and/or by adding 0.5–1% Triton X-100. If strains without pLysS were used, cells were lysed by sonication.

Cell debris was removed by centrifugation at 24,500×g for about 45 min at 4° C. Glutathione Sepharose 4B (Pharmacia LKB, Gaithersburg, Md.) affinity resin beads were washed with PBS and then added to the cell supernatant, employing 1 ml of a 50% bead slurry per liter of supernatant. The suspension was incubated at room temperature or 4° C. for ~1 hr with gentle shaking. The supernatant was decanted after centrifugation at 2000×g for about one minute. The beads were then washed three times with PBS containing 1 mM DTT, 0.5 mM EDTA and 0.5–1% Triton X-100 followed by washing two times with PBS containing 1 mM DTT and 0.5 mM EDTA. The beads were decanted and the fusion protein product eluted twice with a solution of 50 mM Tris, pH 8.0, 15 mM reduced glutathione, 1 mM DTT and 0.5 mM EDTA.

Figure 2:
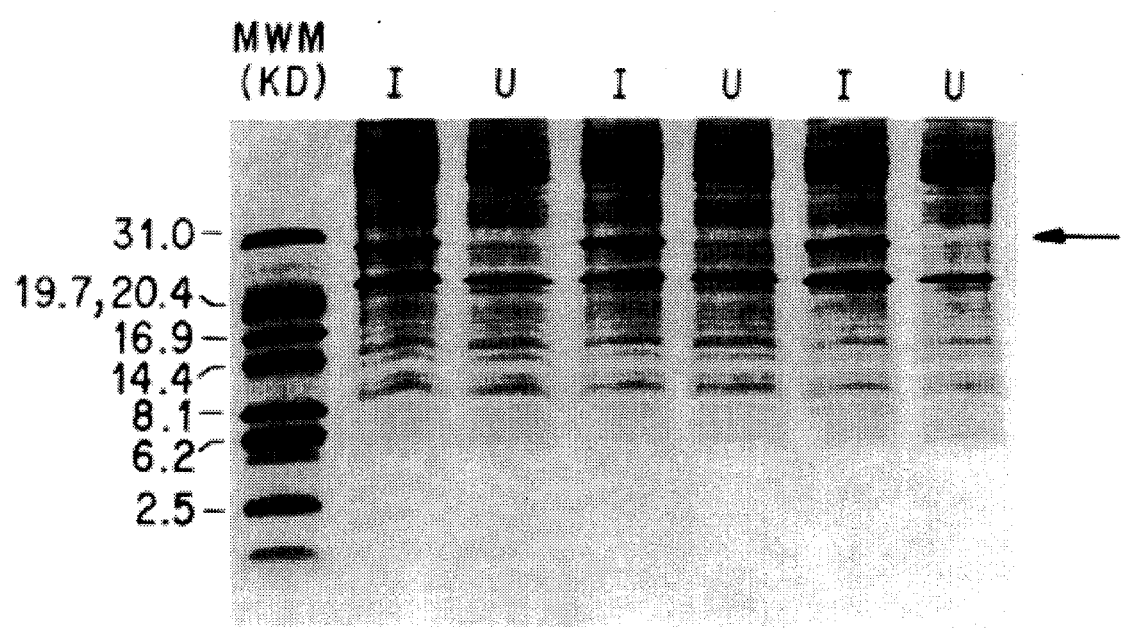
FIG. 2 indicates the induction profile of a 34-mer peptide fused with glutathione-S-transferase as shown by SDS- PAGE. MWM indicates molecular weight markers. The arrow indicates the position of an approximately 31 kDa recombinant polypeptide found in the induced cells (I) but undetectable in uninduced (U) cells.
Figure 3:
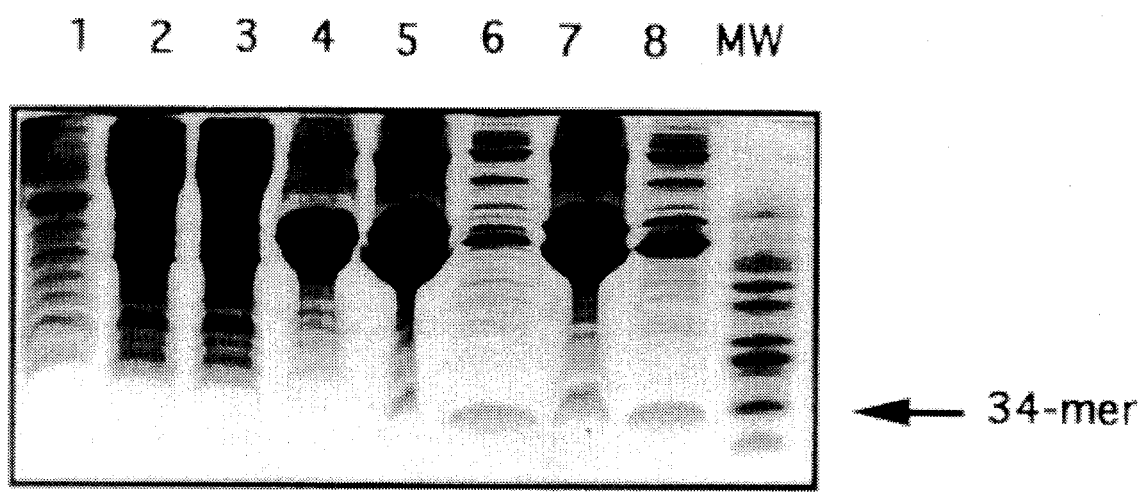
FIG. 3 shows the progress of the purification and cleavage of a glutathione-S-transferase fused 34 amino acid (34-mer) polypeptide as followed on SDS-PAGE. Lane 1: lysed cells pelleted; lanes 2 and 3: supernatant from the lysed cells; lane 4: the fusion protein on glutathione-agarose beads (glutathione affinity purification); lanes 5 and 7: the GST-34 bound to beads prior to cleavage; lanes 6 and 8: the GST on beads after cleaving with TEV proteinase, the arrow indicating the free 34-mer peptide.
Figure 4:
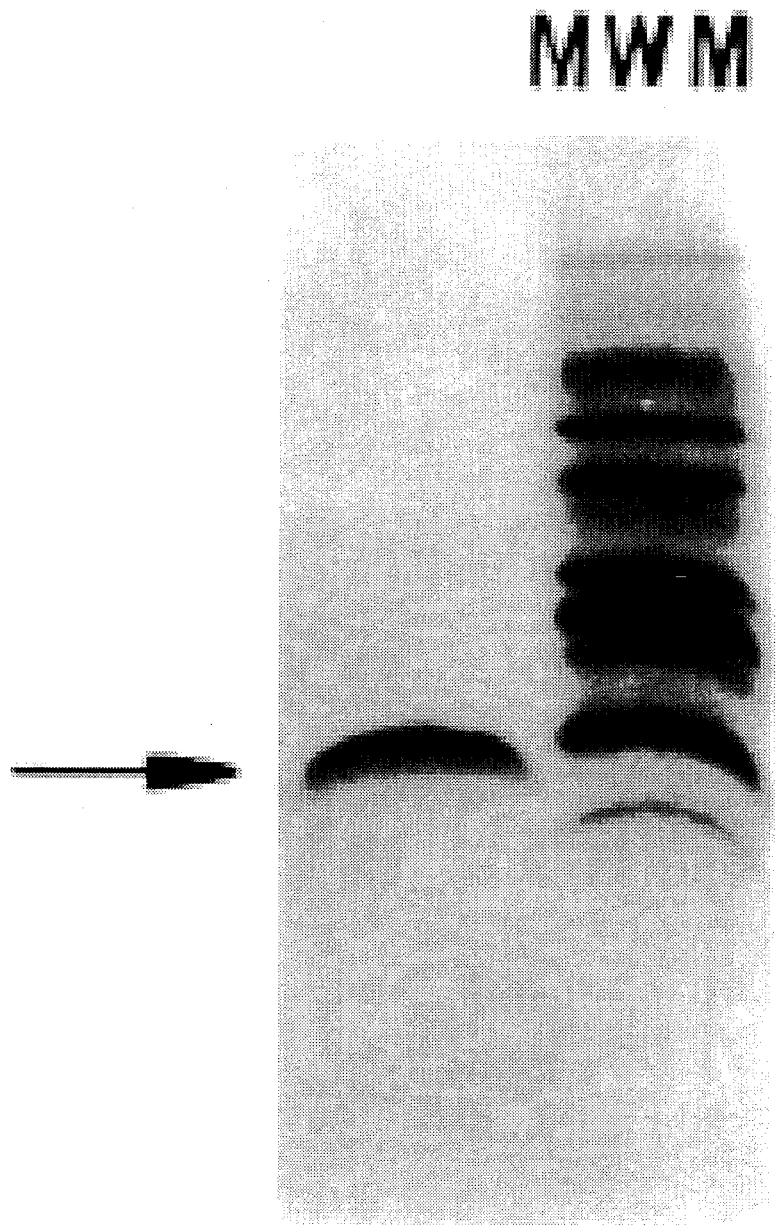
FIG. 4 shows the 34-mer peptide after purification by ion exchange chromatography and gel filtration, lane 2. Lane 1 shows molecular weight markers.
Figure 5:
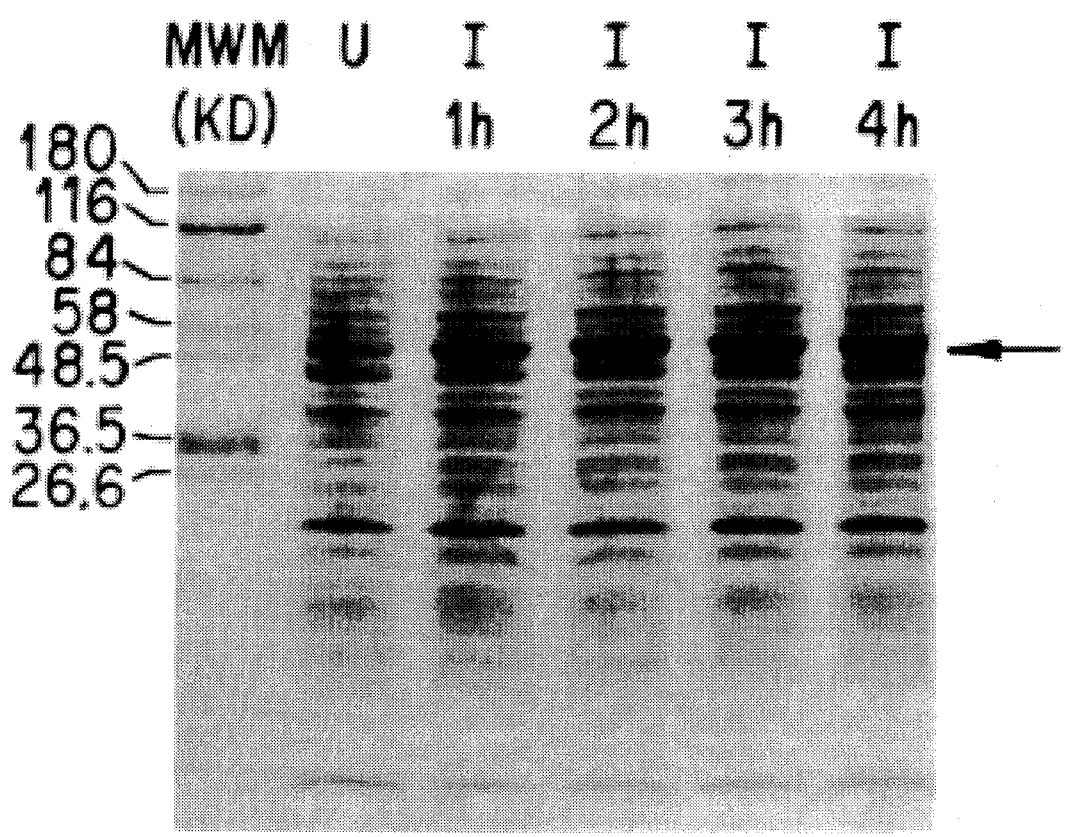
FIG. 5 shows the induction profile of glutathione-S-transferase 27k TEV $NI_a$ proteinase GST/27k fusion protein on SDS-PAGE. The fusion protein, molecular weight ~54 kDa, position is indicated by the arrow. Columns labeled U are uninduced, I are induced. A concurrently run gel with standard molecular weight markers as indicated is shown at the left. Times after induction (1 hr→4hr) are shown at the top of each gel.
Figure 6:
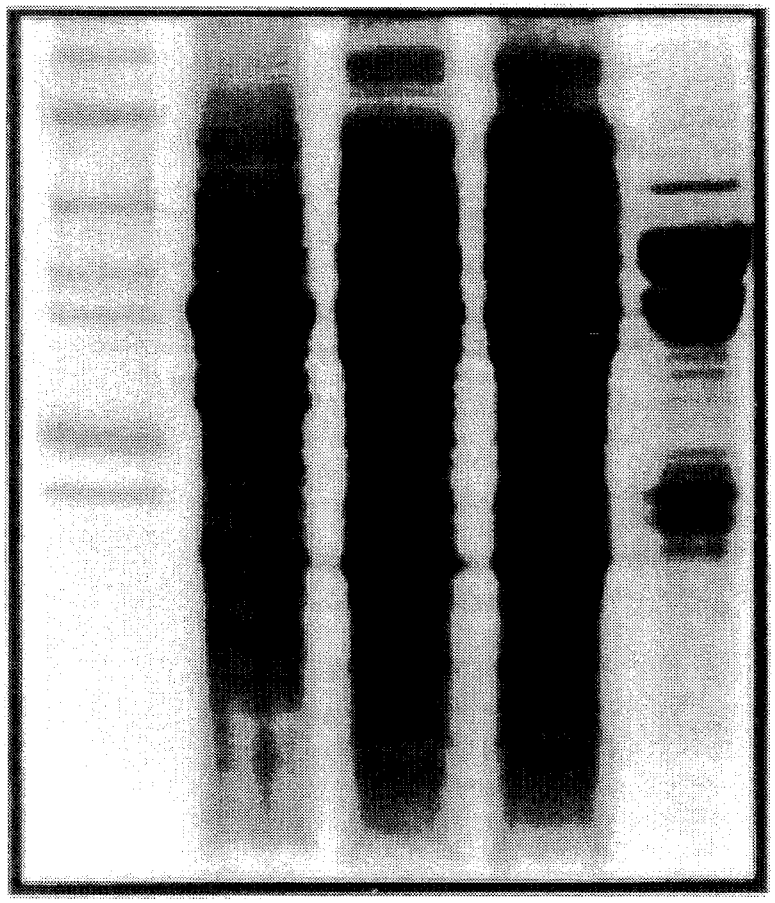
FIG. 6 shows the purification of GST/27k fusion as indicated by SDS-PAGE. Lane 1 is the pellet from lysed cells which had been induced; lane 2 and 3 the supernatant from the lysed cells which had been induced; lane 4 is eluted GST/27k TEV proteinase showing a typical doublet.

The eluate was analyzed by SDS-PAGE. The induction profile of the fusion protein is shown in FIG. 5. Protein products remaining at different steps in the purification were separated on SDS-PAGE as shown in FIG. 6. The fusion protein appeared on the gel as a doublet, differing by several kDa. This doublet band is typical in preparations of TEV proteinase. Preparations were active, based on the ability to cleave known TEV substrates.

After isolation, the yield of purified proteinase was typically in the range of 5 mg/liter of culture.

The fusion protein was aliquoted and stored at −80° C. in 20% glycerol under argon.

Induction of Protein Expression Using pGEX-6HisPro or pTRC-7HisPro

Either of these plasmids were used to express proteins. Induction of protein expression and lysis of bacteria were identical to pGST/27K. Purification of proteinase employed affinity chromatography using nickel agarose affinity chromatograph.

Figure 10:
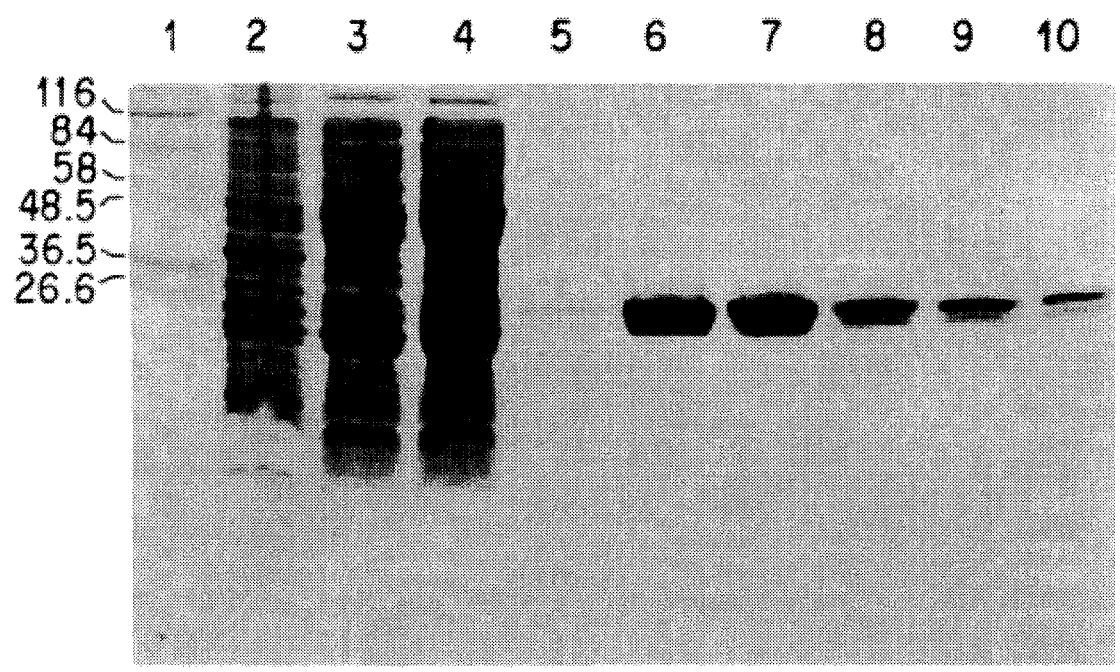
FIG. 10 shows the purification of histidine-tagged TEV after nickel agarose column purification. Lane 1: molecular weight markers; lane 2: pellet after cell lysis; lane 3: supernatant after cell lysis; lane 4: nickel-agarose column flow-through; lane 5: column flow-through after washing; lanes 6–10: several fractions eluted with 75 mM imidazole, pH 7.0.

Growth conditions and cell lysis for the histidine-tagged TEV proteinases from pGEX-6hispro and pTRC-7hispro were the same as for the GST-tagged proteinase. Absorption to a Nickel NTA-agarose resin was in accordance with the manufacturer's instructions (Quiagen, Chatsworth, Calif.). The His-tagged TEV proteinase was eluted with 75 mM imidazole, pH 7.0. Yields were comparable to the GST-tagged TEV proteinase. SDS-PAGE analysis of a typical purification of histidine-tagged TEV protease is shown in FIG. 10.

The lysate was treated with DNAse (250 µg/ml) for 15 min at 37° C. and centrifuged at 8000×g. The supernatant was made 0.3M in NaCl. The supernatant was passed through a Ni-agarose affinity column and the histidine-tagged proteinase bound to this matrix. The column was washed with 8 bed volumes of a solution of 10 mM Tris-HCl (pH 7.5), 0.3M NaCl and 10 mM imidazol, followed by 5 bed volumes of 50 mM sodium phosphate buffer (pH 6.75), 0.3M NaCl and 50 mM imidazol. The bound proteinase was eluted from the column by competing with 25 mM sodium phosphate buffer (pH 8.0), 0.3M NaCl, and 100 mM imidazol. The proteinase was collected to afford a typical yield of 4–5 mg from 500 ml of culture.

EXAMPLE 2

The following is an example of the expression and purification of a relatively small polypeptide fused with glutathione-S-transferase. Tobacco etch virus proteinase is employed to selectively cleave the polypeptide from the fusion partner, GST. The example is illustrated with *E. coli* TG1 and with *E. coli* BL21, which is a strain deficient in the ion protease and in OmpT encoded outer membrane protease.

Isolation of 34-mer Polypeptide

A 34 amino acid sequence (34-mer) corresponding to the C-terminal domain of yeast transcriptional activator GAL4 was cloned into pGEX-CS as an NcoI-BamHI fragment obtained by PCR amplification. The 34-mer is encoded by nucleotide sequences from position 841 through position 874 of the GAL4 protein sequence (Leuther and Johnson, 1992).

*E. coli* cells (TG1 or BL21) containing the plysS plasmid, transformed with the modified pGEX-CS vector were inoculated into L-Broth (+Ampicillin and Chloramphenicol). Alternatively, 2X YT was employed as the growth medium. The cells were grown overnight at 30° C., then diluted 1:10 into L-Broth (+Ampicillin, Chloramphenicol). After reaching a density of $OD_{600}$=~0.6, or $OD_{600}$=3 to 4 if grown in a fermenter, the remaining culture was induced by adding IPTG to 0.3 mM and grown for an additional 2 to 4 hours.

The cells were harvested by centrifugation and resuspended in 1/100 volume of PBS (pH 7.3) to which protease inhibitors 1 mM PMSF, 1 µg/ml Leupeptin, 1 µg/ml Pepstatin A were added. Cells were lysed by freeze thawing and/or by adding Triton X-100 to 0.5 to 1%. If cells did not carry the pLysS plasmid, cells were disrupted by sonication.

In large scale preparations of 5 liters of cells or more, the lysed cells were treated with DNase I in the presence of 10 mM MgCl$_2$. In all preparations, cell debris and DNA was removed by centrifugation in Oakridge tubes, typically requiring up to 45 minutes at 24,500×g at 4° C. for large scale preparations.

GST beads (Glutathione Sepharose 4B, Pharmacia) were washed in PBS before adding to the supernatant, employing 1 ml of a 50% bead slurry per liter of *E. coli* culture. The beads were incubated at room temperature for ~1 hour with gentle shaking, centrifuged briefly and the supernatant decanted. The beads were then washed 3× in PBS+0.5% to 1% Triton X-100 and 2× in PBS. The last wash was decanted and 200 μl of TEV proteinase (or GST-TEV Proteinase fusion) per 1 liter of original *E. coli* culture added to the bead slurry. Protease inhibitors may be added to the reaction mixture at this point.

Incubation was continued for 1–2 hrs at 30° C. with gentle shaking at 200 rpm in an air shaker. After a brief spin (2000×g, 1 min), the supernatant containing the cleaved protein was collected. Beads were washed in a small volume of PBS to recover more of the cleaved protein. Samples were then analyzed by SDS-PAGE and/or Western Blot. After cleaving the 34-mer from GST on the beads, supernatant was loaded onto a MonoQ column (Pharmacia). The 34-mer eluted between 800–900 mM NaCl. The bulk of the TEV proteinase eluted at lower salt concentrations. Remaining trace proteins were removed by gel filtration using a Superdex 75 (Pharmacia) column. The 34-mer was the single, last peptide eluting.

The TEV proteinase recognition sequence in pGEX-CS3 is glu asn leu tyr phe gln gly (SEQ ID NO:11). The proteinase cleaved between gln and gly. The met codon is part of the NcoI site used to clone the DNA encoding the 34-mer. The 34-mer as isolated contained gly ala met residues at the N-terminus.

Production of the GST/34-mer fusion protein in *E. coli* was 5–10 mg/l. Yield of pure 34-mer after purification was 200–300 μg/l.

EXAMPLE 3

This example illustrates expression of a large protein in an *E. Coli* cell using the pGEX-CS3 vector of FIG. 8.

Isolation of GAL4 Protein

An NcoI site was introduced at the start codon (position 443–445 from the 5'-end of sequence published in Laughon and Gesbelaud (1984) using site-directed mutagenesis. The GAL4 gene was cut with HindIII at the 3' end and filled in to generate a blunt end. The gene was then cut with NcoI. The NcoI-blunt fragment was cloned into pGEX-CS that had been cut with NcoI and SmaI.

Expression, isolation of the fusion protein and cleavage of the full length GAL4 protein from GST, was accomplished by the same procedures employed for purification and isolation of the 34-mer, except that cells were grown at 30° C. rather than at 37° C.

While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that numerous polypeptides may be isolated and purified using this system and that it will be particularly useful for protease sensitive polypeptides. Additionally, while only particular carriers have been demonstrated with the fusions, there are numerous other carriers, including antigenic segments which could be bound to affinity columns, which could be employed. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for or teach methodology, techniques and/or compositions employed herein.

Allison, Johnston, Dougherty, *Virology* 154, 9–20 (1986).

Bachmair, A., Finley, D. and Varshausky, A. (1986) "In vivo half-life of a protein is a function of its amino terminal residue" *Science* 234, 179–186.

Dahlman, K., Stromstedt, P.-E., Rae, C., Jornvall, H., Flock, J.-I., Carlstedt-Duke, J. and Gustafsson, J. A., "High Level Expression in *Escherichia coli* of the DNA-binding Domain of the Glucocorticoid Receptor in a Functional Form Utilizing Domain-Specific Cleavage of a Fusion Protein", *J. Biol Chem.* 264, 804–809 (1989).

Dougherty, W. G., Cary, S. M. and Parks, T. D. 1989. "Molecular genetic analysis of a plant virus polyprotein cleavage site: A model", *Virology* 171, 356–364.

Guan, K. and Dixon, J. E., "Eukaryotic Proteins Expressed in *Escherichia coli*: An Improved Thrombin Cleavage and Purification Procedure of Fusion Proteins with Glutathione S-Transferase", *Anal. Biochem.* 192, 262–267 (1991).

Laughon and Gesbelaud, *Mol. Cell. Biol.* 4, 260- (1984).

Leuther, K. K. and Johnson, S. A., (1992) *Science* 256, 1333–1335.

Jarvis, D. L. and Carrington, J. C., U.S. Pat. No. 5,179,007 Jan. 12, 1993).

Maniatis, T., Fritch, E. F. and Sambrook, J. Molecular Cloning, Cold Spring Harbor, N.Y., 1982.

Parks, T. D. and Dougherty, W. G. 1991. "Substrate recognition by the NIa proteinase of two potyviruses involves multiple domains: characterization using genetically engineered hybrid proteinase molecules", *Virology* 182, 17–27.

Parks, T. D., Smith, H. A. and Dougherty, W. G. 1992. "Cleavage profiles of tobacco etch derived substrates mediated by precursor and processed forms of the TEV NIa proteinase. *J. Gen. Virol.* 73, 149–155.

Taylor, M. D. and Drickamer, K., "Carbohydrate-Recognition Domains as Tools for Rapid Purification of Recombinant Eukaryotic Proteins", *Biochem J.* 274, 575–580 (1991).

Waldenstrom, M. Holmgren, E., Attersand, A., Kalderen, C., Lowenadler, B., Raden, B. Hansson and Pohl, G., "Synthesis and Secretion of a Fibrinolytically Active Tissue-Type Plasmiogen Activator Variant in *Escherichia coli*", Gene 99, 243–248 (1991).

What is claimed is:

1. A method of producing and isolating a recombinant polypeptide, comprising:

transforming a yeast or gram-negative bacterial cell with a recombinant DNA molecule that comprises a first DNA encoding a matrix-binding protein, a second DNA encoding a tobacco etch virus NIa proteinase cleavage site, and a third DNA encoding a polypeptide;

binding the expressed fusion protein to a matrix to a matrix that selectively binds the matrix-binding protein; and contacting matrix bound fusion protein with active, soluble recombinant 27 kDa tobacco etch virus NIa proteinase fused with a tag that selectively binds to an adsorbent material;

wherein said proteinase selectively cleaves said cleavage site to release the recombinant polypeptide.

2. The method of claim 1 wherein the transformed bacterial host cell belongs to the genus Escherichia, Klebsiella, Erwinia, Salmonella or Serratia.

3. The method of claim 1 wherein the transformed bacterial host cell is *Escherichia coli* TG1 or BL21.

4. The method of claim 1 wherein the transformed yeast cell host is *S. cerevisiae*.

5. The method of claim 1 wherein the matrix-binding protein comprises a carbohydrate recognition region of galactose specific lectin, an immoglobulin binding protein, maltose binding protein or polyhistidine.

6. The method of claim 1 wherein the matrix-binding protein is glutathione-S-transferase.

7. The method of claim 1 wherein the proteinase cleavage site includes the amino acid sequence of SEQ ID NO:1, SEQ ID NO:2, SEQ ID NO:3 or SEQ ID NO:11.

8. The method of claim 1 further comprising incubating the cell contents with one or more cell protease inhibitors.

9. The method of claim 8 wherein the cell protease inhibitor is leupeptin, pepstalin A, bestatin, ethylenediaminetetraacetic acid, phenylmethylsulfonyl fluoride, N-α-p-tosyl-L-lysine chloromethyl ketone or aprotinin.

10. A method of claim 1 wherein the matrix bound protein is contacted with histidine-tagged 27 kDa tobacco etch virus NIa proteinase.

11. The method of claim 10 further including releasing the recombinant polypeptide while retaining the histidine-tagged 27 kDa tobacco etch virus NIa proteinase.

12. A method of overproducing a recombinant, active 27 kDa tobacco etch virus proteinase comprising:

transforming a yeast or gram-negative bacterial cell with a recombinant vector which comprises a DNA encoding a 27 kDa tobacco etch virus proteinase linked with a DNA encoding a fusion partner polypeptide that selectively binds to an affinity matrix; and culturing the transformed cell to express a fusion protein that undergoes self-proteolysis to produce soluble, active 27 kDa NIa tobacco etch virus proteinase.

13. The method of claim 12 wherein the proteinase comprises a 27 kDa amino acid sequence encoded by the nucleic acid sequence of FIG. 1 (SEQ ID NO:4).

14. The method of claim 12 wherein the fusion partner polypeptide is glutathione-S-transferase, alkaline phosphatase, maltose binding protein, β-galactosidase or polyhistidine.

15. The method of claim 12 wherein the recombinant vector comprises the sequence of FIG. 11A (SEQ ID NO:12 connected 3' to SEQ ID NO:4 connected 3' to SEQ ID NO:13), FIG. 11B (SEQ ID NO:15 connected 3' to SEQ ID NO:4 connected 3' to SEQ ID NO:13), or FIG. 11C (SEQ ID NO:17 connected 3' to SEQ ID NO:4 connected 3' to SEQ ID NO:18).

16. Recombinant active 27 kD tobacco etch virus NIa proteinase prepared by the method of claim 12.

17. A method of overproducing recombinant tobacco etch virus 27 kDa NIa proteinase, comprising:

transforming an *E. coli* or *S. cerevisiae* cell with a recombinant vector that includes a DNA encoding a matrix-binding protein, a DNA encoding a tobacco etch virus cleavage site, and a 27k DNA segment of tobacco etch virus proteinase NIa; and culturing the transformed cell to express a fusion protein that undergoes self-proteolysis at the tobacco etch virus NIa proteinase cleavage site to produce soluble, active 27 kD NIa tobacco etch virus proteinase.

18. An isolated, purified recombinant soluble 27 kDa protease produced by the method of claim 17 that specifically cleaves tobacco etch virus NIa proteinase cleavage site.

19. A purified, active, recombinant tobacco etch virus 27 kDa proteinase NIa.

20. A recombinant 27 kDa tobacco etch virus proteinase NIa fused with alkaline phosphatase, β-galactosidase, glutathione-S-transferase, or polyhistidine.

* * * * *

UNITED STATES PATENT AND TRADEMARK OFFICE
CERTIFICATE OF CORRECTION

PATENT NO. : 5,532,142
DATED : July 2, 1996
INVENTOR(S) : Stephen A. Johnston and William G. Dougherty It is certified that error appears in the above-indentified patent and that said Letters Patent is hereby corrected as shown below:

```
Col. 23:
In claim 1, line 9, delete "to a matrix".

Col. 23:
In claim 2, lines 19 and 20, Escherichia, Klebsiella, Erwinia,
Salmonella and Serratia, should be italicized.

Col. 23:
In claim 9, line 37, delete "pepstalin A" and substitute --pepstatin
A--.

Col. 23:
In claim 10, line 40, delete "A" and substitute --The--.
```

Signed and Sealed this

Twenty-second Day of October, 1996

*Attest:*

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
( A ) LENGTH: 7 amino acid residues
( B ) TYPE: amino acid
( C ) STRANDEDNESS: single
( D ) TOPOLOGY: linear ( x i ) SEQUENCE DESCRIPTION: SEQ ID NO:1:

Glu Xaa Xaa Tyr Xaa Gln Ser
1               5

( 2 ) INFORMATION FOR SEQ ID NO:2:

( i ) SEQUENCE CHARACTERISTICS:
( A ) LENGTH: 7 amino acid residues
( B ) TYPE: amino acid
( C ) STRANDEDNESS: single
( D ) TOPOLOGY: linear ( x i ) SEQUENCE DESCRIPTION: SEQ ID NO:2:

Glu Xaa Xaa Tyr Xaa Gln Gly
1               5

( 2 ) INFORMATION FOR SEQ ID NO:3:

( i ) SEQUENCE CHARACTERISTICS:
( A ) LENGTH: 7 amino acid residues
( B ) TYPE: amino acid
( C ) STRANDEDNESS: single
( D ) TOPOLOGY: linear ( x i ) SEQUENCE DESCRIPTION: SEQ ID NO:3:

Glu Asn Leu Tyr Phe Gln Gly
1               5

( 2 ) INFORMATION FOR SEQ ID NO:4:

( i ) SEQUENCE CHARACTERISTICS:
( A ) LENGTH: 726 base pairs
( B ) TYPE: nucleic acid
( C ) STRANDEDNESS: single
( D ) TOPOLOGY: linear ( x i ) SEQUENCE DESCRIPTION: SEQ ID NO:4:

| | | | | | | |
|---|---|---|---|---|---|---|
| GGAGAAAGCT | TGTTTAAGGG | ACCACGTGAT | TACAACCCGA | TATCGAGCAC | CATTTGTCAT | 60 |
| TTGACGAATG | AATCTGATGG | GCACACAACA | TCGTTGTATG | GTATTGGATT | TGGTCCCTTC | 120 |
| ATCATTACAA | ACAAGCACTT | GTTTAGAAGA | AATAATGGAA | CACTGTTGGT | CCAATCACTA | 180 |
| CATGGTGTAT | TCAAGGTCAA | GAACACCACG | ACTTTGCAAC | AACACCTCAT | TGATGGGAGG | 240 |
| GACATGATAA | TTATTCGCAT | GCCTAAGGAT | TTCCCACCAT | TTCCTCAAAA | GCTGAAATTT | 300 |
| AGAGAGCCAC | AAAGGGAAGA | GCGCATATGT | CTTGTGACAA | CCAACTTCCA | AACTAAGAGC | 360 |
| ATGTCTAGCA | TGGTGTCAGA | CACTAGTTGC | ACATTCCCTT | CATCTGATGG | CATATTCTGG | 420 |
| AAGCATTGGA | TTCAAACCAA | GGATGGGCAG | TGTGGCAGTC | CATTAGTATC | AACTAGAGAT | 480 |
| GGGTTCATTG | TTGGTATACA | CTCAGCATCG | AATTTCACCA | ACACAAACAA | TTATTTCACA | 540 |
| AGCGTGCCGA | AAAACTTCAT | GGAATTGTTG | ACAAATCAGG | AGGCGCAGCA | GTGGGTTAGT | 600 |

GGTTGGCGAT TAAATGCTGA CTCAGTATTG TGGGGGGGCC ATAAAGTTTT CATGAGCAAA       660

CCTGAAGAGC CTTTTCAGCC AGTTAAGGAA GCGACTCAAC TCATGAATGA ATTGGTGTAC       720

TCGCAA                                                                   726

( 2 ) INFORMATION FOR SEQ ID NO:5:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

GAGAATCTTT ATTTTCAGGG CGCCATGGAT CCCGGGCGAA TTC                          43

( 2 ) INFORMATION FOR SEQ ID NO:6:

( i ) SEQUENCE CHARACTERISTICS:
        ( A ) LENGTH: 12 amino acid residues
        ( B ) TYPE: amino acid
        ( C ) STRANDEDNESS: single
        ( D ) TOPOLOGY: linear ( x i ) SEQUENCE DESCRIPTION: SEQ ID NO:6:

Glu  Asn  Leu  Tyr  Phe  Gln  Gly  Ala  Met  Asp  Pro  Gly
 1              5                        10

( 2 ) INFORMATION FOR SEQ ID NO:7:

( i ) SEQUENCE CHARACTERISTICS:
        ( A ) LENGTH: 43 amino acid residues
        ( B ) TYPE: amino acid
        ( C ) STRANDEDNESS: single
        ( D ) TOPOLOGY: linear ( x i ) SEQUENCE DESCRIPTION: SEQ ID NO:7:

Gly  Ala  Thr  Asp  Gln  Thr  Ala  Tyr  Asn  Ala  Phe  Gly  Ile  Thr  Thr  Gly
 1              5                        10                       15

Met  Phe  Asn  Thr  Thr  Thr  Met  Asp  Asp  Val  Tyr  Asn  Tyr  Leu  Phe  Asp
               20                        25                       30

Asp  Glu  Asp  Thr  Pro  Pro  Asn  Pro  Lys  Lys  Glu
               35                        40

( 2 ) INFORMATION FOR SEQ ID NO:8:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GTGGATCCAT GGCGCCCTGA AAATAAAGAT TCTCGAGATG                              40

( 2 ) INFORMATION FOR SEQ ID NO:9:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

TATCCATGGC CCCTATACTA GG                                                 22

( 2 ) INFORMATION FOR SEQ ID NO:10:

( i ) SEQUENCE CHARACTERISTICS:
        ( A ) LENGTH: 6 amino acid residues
        ( B ) TYPE: amino acid
        ( C ) STRANDEDNESS: single
        ( D ) TOPOLOGY: linear ( x i ) SEQUENCE DESCRIPTION: SEQ ID NO:10:

Glu Asn Lys Tyr Phe Gln
 1               5

( 2 ) INFORMATION FOR SEQ ID NO:11:

( i ) SEQUENCE CHARACTERISTICS:
        ( A ) LENGTH: 7 amino acid residues
        ( B ) TYPE: amino acid
        ( C ) STRANDEDNESS: single
        ( D ) TOPOLOGY: linear ( x i ) SEQUENCE DESCRIPTION: SEQ ID NO:11:

Glu Asn Leu Tyr Phe Gln Gly
 1               5

( 2 ) INFORMATION FOR SEQ ID NO:12:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

CCAAAATCGG ATCTGGTTCC GCGTGGATCC AGCTTG                    36

( 2 ) INFORMATION FOR SEQ ID NO:13:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

TACTCGCAAT GAGAATTC                                        18

( 2 ) INFORMATION FOR SEQ ID NO:14:

( i ) SEQUENCE CHARACTERISTICS:
        ( A ) LENGTH: 15 amino acid residues
        ( B ) TYPE: amino acid
        ( C ) STRANDEDNESS: single
        ( D ) TOPOLOGY: linear ( x i ) SEQUENCE DESCRIPTION: SEQ ID NO:14:

Pro Lys Ser Asp Leu Val Pro Arg Gly Ser Ser Leu Tyr Ser Gln
 1               5                    10                 15

( 2 ) INFORMATION FOR SEQ ID NO:15:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

GAGAATCTTT ATTTTCAGGG CGCCATGGGA TCCCATCACC ATCACCATCA CGGAGAAAGC    60

TTG    63

( 2 ) INFORMATION FOR SEQ ID NO:16:

( i ) SEQUENCE CHARACTERISTICS:
            ( A ) LENGTH: 24 amino acid residues
            ( B ) TYPE: amino acid
            ( C ) STRANDEDNESS: single
            ( D ) TOPOLOGY: linear ( x i ) SEQUENCE DESCRIPTION: SEQ ID NO:16:

Glu Asn Leu Tyr Phe Gln Gly Ala Met Gly Ser His His His His His
 1               5                  10                 15
His Gly Glu Ser Leu Tyr Ser Gln
            20

( 2 ) INFORMATION FOR SEQ ID NO:17:

( i ) SEQUENCE CHARACTERISTICS:
            ( A ) LENGTH: 63 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:17:

AGGAAACAGA CCATGATGCA CCATCACCAT CACCATCACG CCATGGGAGA AAGCTTGTTT    60

AAG    63

( 2 ) INFORMATION FOR SEQ ID NO:18:

( i ) SEQUENCE CHARACTERISTICS:
            ( A ) LENGTH: 32 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:18:

TTGGTGTACT CGCAATGAAA GCTTGGGAGC TC    32

( 2 ) INFORMATION FOR SEQ ID NO:19:

( i ) SEQUENCE CHARACTERISTICS:
            ( A ) LENGTH: 17 amino acid residues
            ( B ) TYPE: amino acid
            ( C ) STRANDEDNESS: single
            ( D ) TOPOLOGY: linear ( x i ) SEQUENCE DESCRIPTION: SEQ ID NO:19:

Met Met His His His His His His His Ala Met Gly Glu Ser Leu Phe
 1               5                  10                 15
Lys ( 2 ) INFORMATION FOR SEQ ID NO:20:

( i ) SEQUENCE CHARACTERISTICS:
            ( A ) LENGTH: 5 amino acid residues
            ( B ) TYPE: amino acid
            ( C ) STRANDEDNESS: single
            ( D ) TOPOLOGY: linear ( x i ) SEQUENCE DESCRIPTION: SEQ ID NO:20:

Leu Val Tyr Ser Gln
 1               5